(12) United States Patent
Matsuda et al.

(10) Patent No.: US 6,517,132 B2
(45) Date of Patent: Feb. 11, 2003

(54) MULTIFINGER HAND DEVICE

(75) Inventors: Hiroshi Matsuda, Wako (JP); Kazuhiro Kishimoto, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 38 days.

(21) Appl. No.: 09/824,233

(22) Filed: Apr. 3, 2001

(65) Prior Publication Data

US 2001/0028174 A1 Oct. 11, 2001

(30) Foreign Application Priority Data

Apr. 4, 2000 (JP) .................................... 2000-102019

(51) Int. Cl.$^7$ .............................................. B25J 15/10
(52) U.S. Cl. ......................... 294/106; 901/38; 901/39
(58) Field of Search ....................... 294/88, 106, 111, 294/115, 116, 902, 907; 623/57, 64; 901/36–39

(56) References Cited

U.S. PATENT DOCUMENTS

| | | | | |
|---|---|---|---|---|
| 3,694,021 A | * | 9/1972 | Mullen ........................ 294/106 |
| 3,866,966 A | * | 2/1975 | Skinner ....................... 294/106 |
| 4,351,553 A | * | 9/1982 | Rovetta et al. .............. 294/106 |
| 4,921,293 A | * | 5/1990 | Ruoff et al. ............. 294/106 X |
| 4,986,723 A | * | 1/1991 | Maeda .................... 294/111 X |
| 5,062,673 A | * | 11/1991 | Mimura ................... 294/106 X |
| 5,108,140 A | * | 4/1992 | Bartholet .................... 294/106 |
| 5,437,490 A | * | 8/1995 | Mimura et al. ............. 294/106 |
| 5,447,403 A | * | 9/1995 | Engler .................... 294/111 X |

FOREIGN PATENT DOCUMENTS

JP 8-126984 5/1996

* cited by examiner

Primary Examiner—Johnny D. Cherry
(74) Attorney, Agent, or Firm—Arent Fox Kintner Plotkin & Kahn, PLLC

(57) ABSTRACT

A multifinger hand device has a plurality of finger mechanisms extending from a palm unit. The finger mechanisms include a finger mechanism corresponding to a thumb and other finger mechanisms. Joints of the finger mechanism corresponding to the thumb include a joint closest to the palm unit and having a rotational axis about which the joint is rotatable, the rotational axis extending substantially perpendicularly to the rotational axis of a joint, closest to the palm unit, of one of the other finger mechanisms. The joints, closest to the palm unit, of the other finger mechanisms have respective rotational axes about which the joints are rotatable and which are slightly inclined to each other and extend substantially perpendicularly to a main palm plate of the palm unit. The other finger mechanisms have link mechanisms closest to the palm unit which are fixed to the palm unit with their respective rotational axes being inclined to each other.

20 Claims, 10 Drawing Sheets

MULTIFINGER HAND DEVICE

BACKGROUND OF THE INVENTION

1. Field of the Invention

The present invention relates to a multifinger hand device having a plurality of finger mechanisms.

2. Description of the Related Art

Multifinger hand devices having a structure similar to the human hand structure include a plurality of finger mechanisms extending from a palm unit. Each of the finger mechanisms comprises a plurality of link mechanisms successively joined by a plurality of joints. The link mechanisms have respective actuators for operating, e.g., bending, the corresponding joints. For details, reference should be made to Japanese laid-open patent publication No. 8-126984, for example.

The conventional multifinger hand devices have been disadvantageous in that the direction of movement and the layout of the joints of each of the finger mechanisms are not necessarily suitable for grasping a variety of different objects or workpieces. Therefore, there has been a demand for an improved multifinger hand device.

SUMMARY OF THE INVENTION

It is therefore an object of the present invention to provide a multifinger hand device which is capable of grasping objects or workpieces easily and efficiently.

According to the present invention, a multifinger hand device has a palm unit and a plurality of finger mechanisms extending from said palm unit, each of said finger mechanisms comprising a plurality of link mechanisms successively joined from said panel unit by a plurality of joints. The present invention is basically exemplified in first through third aspects.

According to the first aspect, the finger mechanisms include a finger mechanism corresponding to a thumb (also referred to as "thumb mechanism") and other finger mechanisms. The joints (hereinafter referred to as "first joint"), which are closest to said palm unit, of said thumb mechanism and at least one (also referred to as "specific finger mechanism") of said other finger mechanisms are arranged such that a rotational axis about which said joint, closest to said palm unit, of the thumb mechanism is rotatable and a rotational axis about which said joint, closest to said palm unit, of said specific finger mechanism cross each other, preferably cross each other substantially perpendicularly to each other.

With the arrangement of the first aspect, when both or one of the first joint of the thumb mechanism and the first joint of the specific finger mechanism rotates, the portion of the thumb mechanism which is closer to the tip end thereof than the first joint and the portion of the specific finger mechanism which is closer to the tip end thereof than the first joint are brought into facing relation to each other in one plane. Therefore, the multifinger hand device is capable of easily grasping an object between the thumb mechanism and the specific finger mechanism.

In the first aspect of the present invention, each of the other joints than the first joints of the thumb mechanism and the specific finger mechanism may be of such a structure as having a number of degrees of freedom. If each of the other joints has a one degree of freedom, i.e., if it can be rotated about one rotational axis, then the rotational axis should preferably extend perpendicularly to the rotational axis of the first joint.

According to the second aspect, said finger mechanisms include a finger mechanism corresponding to a thumb (thumb mechanism) and other finger mechanisms, the joints of said other finger mechanisms include first joints closest to said palm unit, said first joints being juxtaposed substantially transversely across said palm unit and having respective rotational axes about which the first joints are rotatable and which are oriented substantially perpendicularly to a flat palm surface of said palm unit, and the link mechanisms of said other finger mechanisms include link mechanisms (also referred to as "first link mechanisms") coupled to said first joints and closest to said palm unit, said link mechanisms being fixed to said palm unit such that transversely central axes thereof are inclined to each other and extend toward respective tip ends of said other finger mechanisms.

With the arrangement of the second aspect, since the other finger mechanisms, i.e., the finger mechanisms juxtaposed substantially transversely across said palm unit, have the rotational axes of their first joints oriented substantially perpendicularly to the flat palm surface of said palm unit, the portions of these finger mechanisms which are closer to the tip ends than the first joints can be turned substantially along the flat palm surface of said palm unit about the first joints. Because the first link mechanisms of the other finger mechanisms are fixed to the palm unit such that their transversely central axes are inclined to each other and extend toward respective tip ends of said other finger mechanisms, the finger mechanisms can be turned about the rotational axes of the first joints in a wide angular range out of physical interference with adjacent ones of the finger mechanisms. Thus, each of the other finger mechanisms and adjacent ones thereof can be rotated about the rotational axes of the first joints in a relatively wide angular range without being rotated through an unnecessarily large angular interval. As a result, the finger mechanisms can easily be brought into postures suitable for grasping variously shaped objects.

In the second aspect, if each of the joints, other than the first joints, of the other finger mechanisms has a one degree of freedom, then the rotational axis of the joint should preferably extend perpendicularly to the rotational axis of the first joint. If each of the joints of the thumb mechanism has a one degree of freedom, then it is preferable that the rotational axis of the first joint of the thumb mechanism closest to the palm unit extend substantially perpendicularly to the rotational axes of the first joints of the other finger mechanisms and the rotational axes of the other joints of the thumb mechanism extend perpendicularly to the rotational axis of the first joint of the thumb mechanism.

According to the third aspect, the finger mechanisms include a finger mechanism corresponding to a thumb (thumb mechanism) and other finger mechanisms, the joints (first joints), which are closest to said palm unit, of said other finger mechanisms being juxtaposed substantially transversely across said palm unit and having respective rotational axes about which the joints are rotatable, said joints being arranged with their rotational axes inclined to each other in a direction substantially perpendicular to a flat palm surface of said palm unit, and spreading radially toward a back of said palm unit.

With the arrangement of the third aspect, since the rotational axes of the joints, closest to the palm unit, of the other finger mechanisms are inclined to each other in a direction substantially perpendicular to a flat palm surface of said palm unit, and spreading radially toward a back of said palm unit, when the joints of the other finger mechanisms which are closer to the tip ends thereof than the first joints are operated to bend their portions closer to the tip ends thereof than the first joints toward the flat palm surface, the tip ends of the finger mechanisms tend to be brought together. Therefore, the multifinger hand device can easily grasp an object with those finger mechanisms.

In the third aspect, as with the second aspect, if each of the joints, other than the first joints, of the other finger mechanisms has a one degree of freedom, then the rotational axis of the joint should preferably extend perpendicularly to the rotational axis of the first joint. If each of the joints of the thumb mechanism has a one degree of freedom, then it is preferable that the rotational axis of the first joint of the thumb mechanism closest to the palm unit extend substantially perpendicularly to the rotational axes of the first joints of the other finger mechanisms and the rotational axes of the other joints of the thumb mechanism extend perpendicularly to the rotational axis of the first joint of the thumb mechanism.

The first through third aspects of the present invention may be combined with each other. If the second aspect is combined with the first aspect, then the first joints, closest to the palm unit, of the other finger mechanisms have their rotational axes juxtaposed substantially transversely across said palm unit in the direction substantially perpendicular to the flat palm surface of the palm unit, and the link mechanisms of the other finger mechanism, which are connected to the first joints and positioned closest to the palm unit, are fixed to the palm unit such that their transversely central axes are inclined to each other and spread radially toward the tip ends of the finger mechanisms.

If the third aspect is combined with the first aspect, then the joints (first joints), closest to the palm unit, of the other finger mechanisms are juxtaposed substantially transversely across said palm unit, and have their rotational axes inclined to each other in the direction substantially perpendicular to the flat palm surface of the palm unit, and spreading radially toward the back of the palm unit.

If the third aspect is combined with the second aspect, then the first joints of the other finger mechanisms have their rotational axes inclined to each other in the direction substantially perpendicular to the flat palm surface of the palm unit, and spreading radially toward the back of the palm unit.

In either one of the first through third aspects of the present invention, said other finger mechanisms should preferably include at least two finger mechanisms which are structurally identical to each other.

The identical finger mechanisms can be switched around or can replace each other. Therefore, the inventory control for those identical finger mechanisms can be facilitated. When either one of the identical finger mechanisms is broken, it can easily be replaced with a new one of the other finger mechanisms.

In either one of the first through third aspects of the present invention, the multifinger hand device may also have a plurality of actuators mounted respectively in said finger mechanisms for rotating the joints of the finger mechanisms. If at least two of the other finger mechanisms are identical in structure to each other and if they incorporate actuators therein, then the identical finger mechanisms including the actuators can be switched around or can replace each other.

For actuating the joints of the finger mechanisms, each of the link mechanisms other than the link mechanisms closest to the tip ends of the finger mechanisms should preferably be combined with a rotary actuator means such as an electric motor for actuating the joint between itself and an adjacent link mechanism, and a rotation transmitting means, including a speed reducer, for transmitting the rotational power from the rotary actuator means to the joint.

The above and other objects, features, and advantages of the present invention will become apparent from the following description when taken in conjunction with the accompanying drawings which illustrate a preferred embodiment of the present invention by way of example.

DETAILED DESCRIPTION OF THE PREFERRED EMBODIMENT

Figure 1:
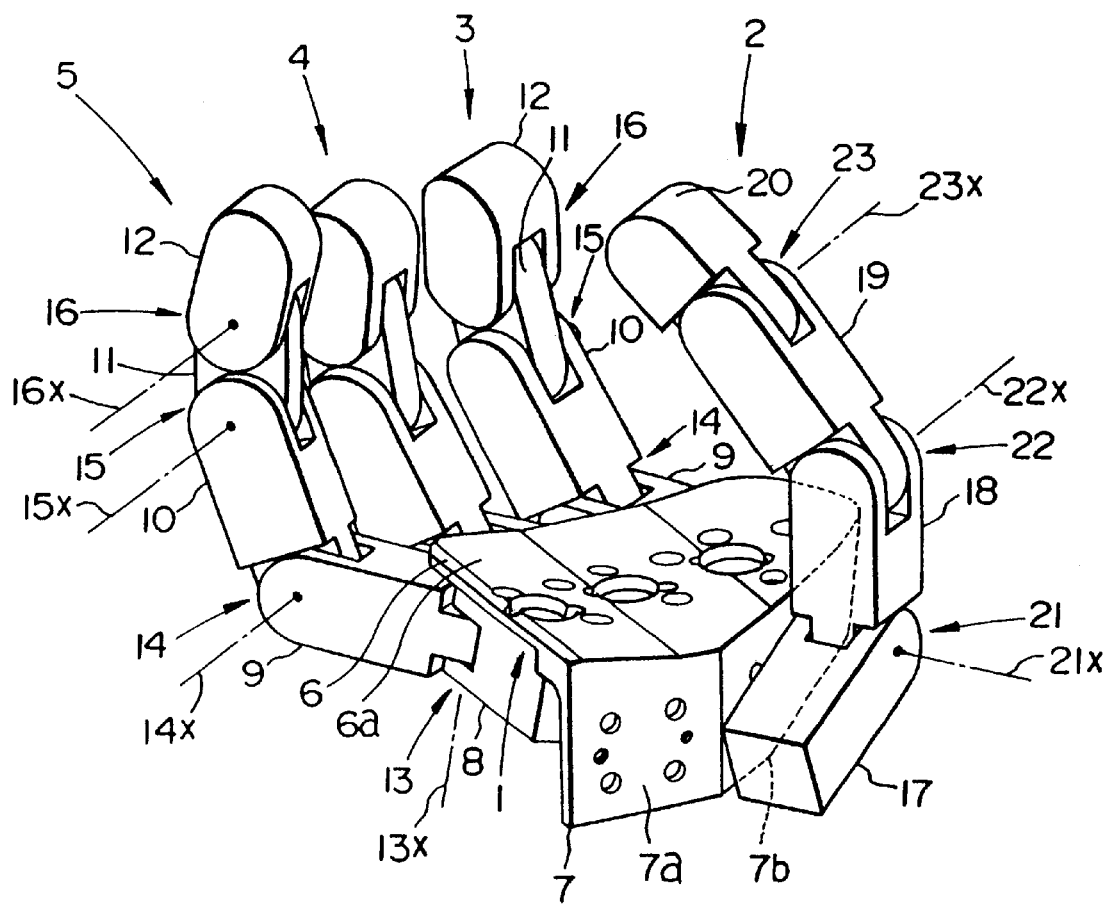
FIG. 1 is a perspective view of a multifinger hand device according to an embodiment of the present invention.
Figure 2:
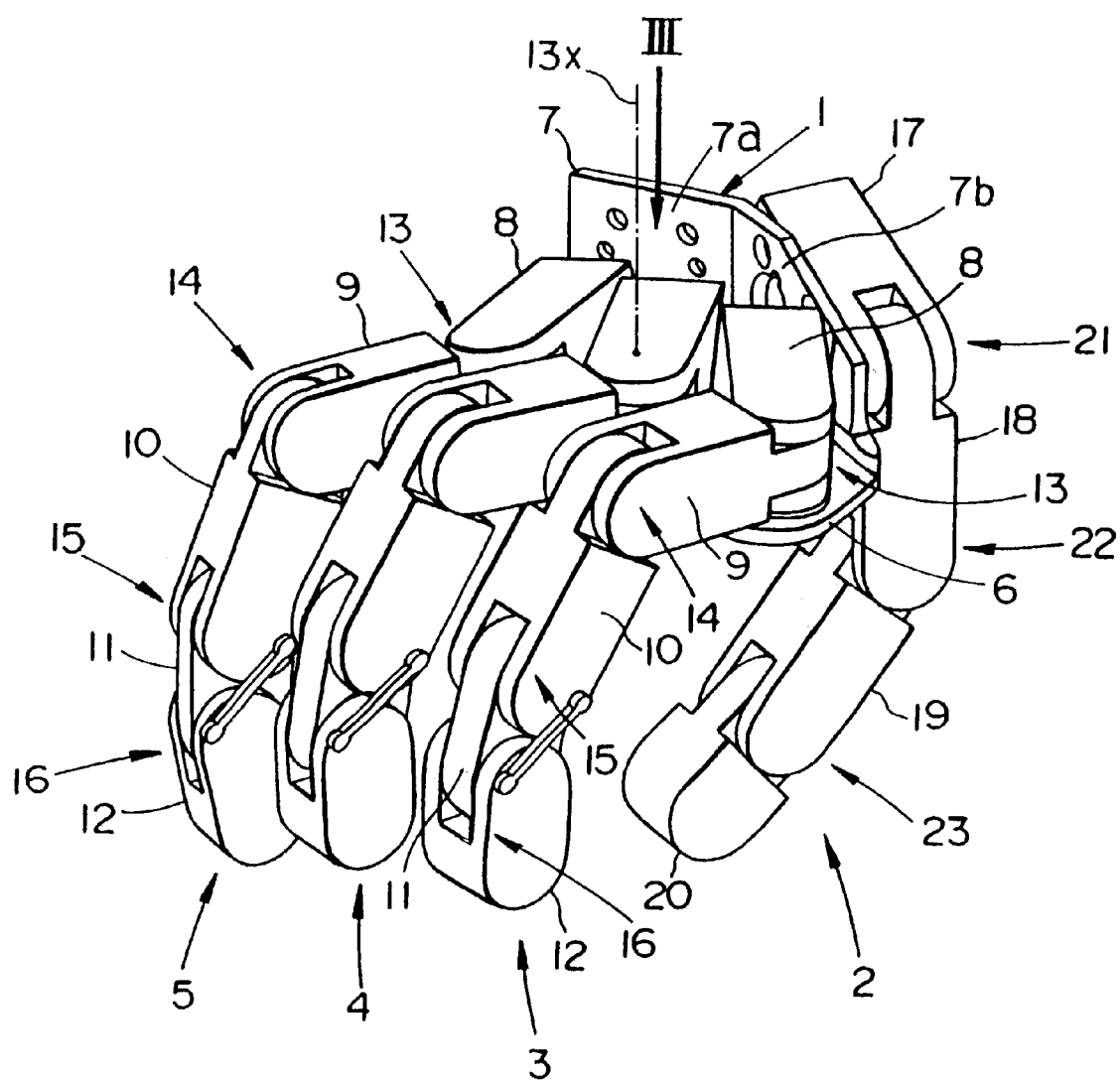
FIG. 2 is a perspective view of the multifinger hand device shown in FIG. 1, the view showing the multifinger hand device at an angle different from the view of the multifinger hand device shown in FIG. 1.

FIGS. 1 and 2 show in perspective a multifinger hand device according to an embodiment of the present invention. FIG. 1 illustrates the multifinger hand device with its palm facing upwardly, and FIG. 2 illustrates the multifinger hand device with its back facing upwardly. In FIGS. 1 and 2, only principal parts of finger mechanisms 2–5 of the multifinger hand device are shown, and other parts thereof such as actuators are omitted from illustration.

As shown in FIGS. 1 and 2, the multifinger hand device comprises a palm unit 1 and a plurality of finger mechanisms 2–5 extending from the palm unit 1. In the illustrated embodiment, there are four finger mechanisms 2–5, with the finger mechanism 2 corresponding to the thumb of a human hand.

The palm unit 1 is constructed of plates including a main palm plate 6 having a flat palm surface 6a (see FIG. 1) and an erected plate 7 extending from a rear end of the main palm plate 6 toward a back of the palm unit 1, i.e., a reverse side of the main palm plate 6, in a direction substantially perpendicular to the main palm plate 6. The finger mechanisms 3–5 are mounted on the reverse side of the main palm plate 6, i.e., the back of the palm unit 1, as shown in FIG. 2.

The erected plate 7 comprises a first partial erected plate 7a extending in a substantially transverse direction of the palm unit 1 and a second partial erected plate 7b disposed on one end of the first partial erected plate 7a and extending obliquely to the first partial erected plate 7a. The first partial erected plate 7a is adapted to be attached to an arm of a robot (not shown), and the second partial erected plate 7b supports the finger mechanism 2 thereon.

Of the finger mechanisms 2–5, the finger mechanisms 3–5 are of an identical structure. Each of the finger mechanisms 3–5 comprises first through fifth link mechanisms 8–12 arranged successively from the palm unit 1 and joined by first through fourth joints 13–16. Since the finger mechanisms 3–5 are identical in structure, some of the finger mechanisms 3–5, i.e., the link mechanisms and the joints of the finger mechanism 4, are not specifically denoted by reference characters for the sake of brevity.

Though the finger mechanisms 3–5 will be described in greater detail later on, each of the joints 13–16 comprises a joint that is rotatable about one rotational axis. In the present embodiment, the rotational axis about which the first joint 13 closest to the palm unit 1 is rotatable extends perpendicularly to the rotational axes, which extend parallel each other, about which the other three, i.e., the second through fourth, joints 14–16, are rotatable.

For example, the finger mechanism 5 will be described in detail below with reference to FIG. 1. The first joint 13 of the finger mechanism 5 allows the second link mechanism 9 to rotate about a rotational axis 13x with respect to the first link mechanism 8. The second joint 14 allows the third link mechanism 10 to rotate about a rotational axis 14x perpendicular to the rotational axis 13x with respect to the second link mechanism 9. The third joint 15 allows the fourth link mechanism 11 to rotate about a rotational axis 15x parallel to the rotational axis 14x with respect to the third link mechanism 10. The fourth joint 16 allows the fifth link mechanism 12 to rotate about a rotational axis 16x parallel to the rotational axis 15x with respect to the fourth link mechanism 11.

The first through fourth joints 13–16 of the finger mechanisms 3, 4 are constructed and rotate in exactly the same manner as the first through fourth joints 13–16 of the finger mechanism 5. The first link mechanisms 8 of the finger mechanisms 3–5 are fixedly mounted on the reverse side of the main palm plate 6 with the rotational axes 13x of the first joints 13 being oriented substantially perpendicularly to the main palm plate 6, and are juxtaposed substantially transversely across the main palm plate 6 (see FIG. 2).

Figure 3:
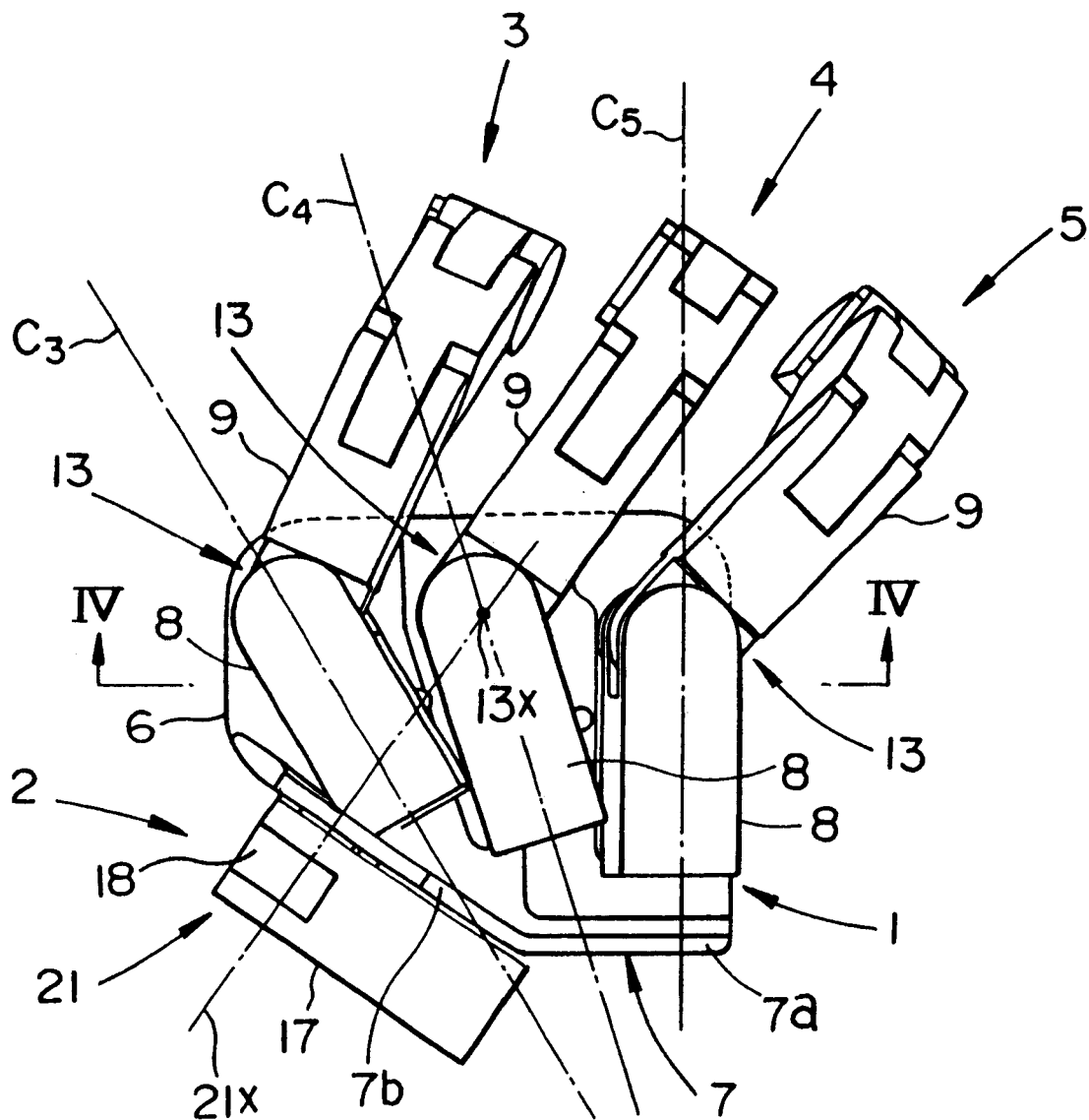
FIG. 3 is a view as viewed in the direction indicated by the arrow III in FIG. 2.
Figure 4:
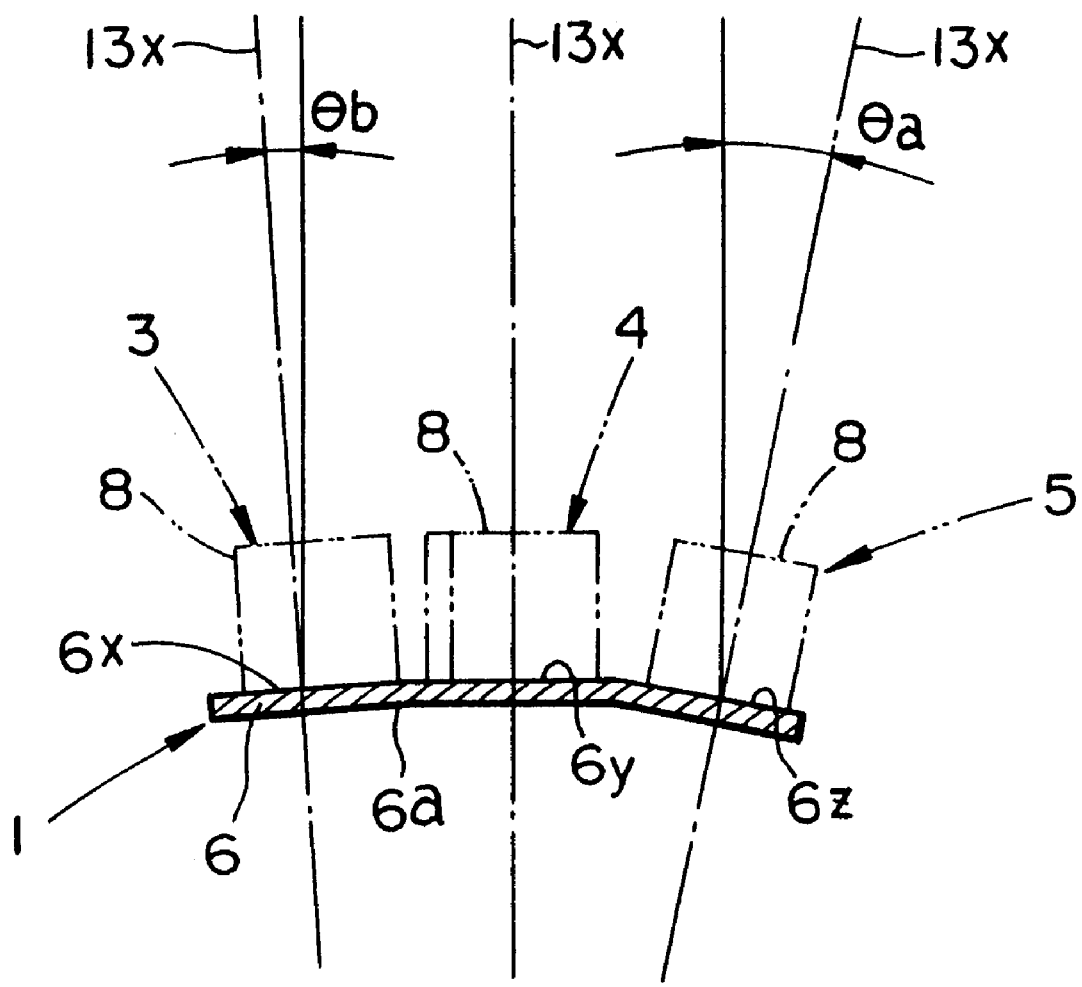
FIG. 4 is a cross-sectional view taken along line IV—IV of FIG. 3.

Details of a structure by which the first link mechanisms 8 of the finger mechanisms 3–5 are attached to the main palm plate 6 will be described below with reference to FIGS. 3 and 4. FIG. 3 shows the multifinger hand device as viewed in the direction indicated by the arrow III in FIG. 2, the view showing the multifinger hand device from its back of the palm unit 1 along the rotational axis 13x of the first joint 13 of the finger mechanism 4. FIG. 4 shows the multifinger hand device in a cross section taken along line IV—IV of FIG. 3. In FIG. 4, the first link mechanisms 8 of the finger mechanisms 3–5 are indicated by the imaginary lines.

As shown in FIG. 3, the first link mechanisms 8 of the finger mechanisms 3–5 are fixedly mounted on the reverse side of the main palm plate 6 such that the first link mechanisms 8 have respective transversely central axes C3, C4, C5 inclined to each other and are spread radially toward the tip ends of the finger mechanisms 3–5. Therefore, when the finger mechanisms 3–5 are extended in the directions of the central axes C3, C4, C5, the finger mechanisms 3–5 are oriented radially from the palm unit 1.

As shown in FIG. 4, the main palm plate 6 is slightly bent across its width toward the flat palm surface 6a. The main palm plate 6 comprises a facet 6x to which the first link mechanism 8 of the finger mechanism 3 is fixed on the reverse side of the main palm plate 6, a facet 6y to which the first link mechanism 8 of the finger mechanism 4 is fixed on the reverse side of the main palm plate 6, and a facet 6z to which the first link mechanism 8 of the finger mechanism 5 is fixed on the reverse side of the main palm plate 6. These facets 6x, 6y, 6z are successively arranged and joined together, and are slightly inclined to each other. With the first link mechanisms 8 of the finger mechanisms 3–5 being fixedly mounted respectively on the facets 6x, 6y, 6z, the rotational axes 13x of the first joints 13, which are closest to the palm unit 1, are also slightly inclined to each other, and extend in a radially spreading fashion in a direction from the palm surface to the back of the palm unit 1. In the present embodiment, the rotational axis 13x of the first joint 13 of the finger mechanism 5 is inclined an angle θa to the rotational axis 13x, which extends vertically in FIG. 4, of the first joint 13 of the finger mechanism 4, and the rotational axis 13x of the first joint 13 of the finger mechanism 3 is inclined an angle θb to the rotational axis 13x of the first joint 13 of the finger mechanism 4. The angle θa is substantially the same as or slightly greater than the angle θb. For example, the angle θa ranges from 5° to 10°, whereas the angle θb is 5°.

As shown in FIGS. 1 and 2, the finger mechanism 2 comprises first through fourth link mechanisms 17–20 that are arranged successively from the palm unit 1 and joined by first through third joints 21–23.

Each of the joints 21–23 of the finger mechanism 2 comprises a joint that is rotatable about one rotational axis, as is the case with the first through third joints 13–15 of the finger mechanisms 3–5. The rotational axis about which the first joint 21 closest to the palm unit 1 is rotatable extends perpendicularly to the rotational axes, which extend parallel each other, about which the other two, i.e., the second and third, joints 22, 23, are rotatable.

As shown in FIG. 1, the first joint 21 of the finger mechanism 2 allows the second link mechanism 18 to rotate about a rotational axis 21x with respect to the first link mechanism 17. The second joint 22 allows the third link mechanism 19 to rotate about a rotational axis 22x perpendicular to the rotational axis 21x with respect to the second link mechanism 18. The third joint 23 allows the fourth link mechanism 20 to rotate about a rotational axis 23x parallel to the rotational axis 22x with respect to the third link mechanism 19.

The first link mechanism 17 of the finger mechanism 2 is fixedly mounted on an outer surface of the second partial erected plate 7b with the rotational axis 21x oriented perpendicularly to the second partial erected plate 7b, i.e., substantially parallel to the main palm plate 6.

As shown in FIG. 3, the finger mechanism 2 is fixed to the second partial erected plate 7b at such a position and attitude that the rotational axis 21x of the first joint 21 extends substantially perpendicularly to the rotational axis 13x of the first joint 13 of the finger mechanism 4.

Structural details of the finger mechanisms 2–5 will further be described below with reference to FIGS. 5 through 8.

Figure 5:
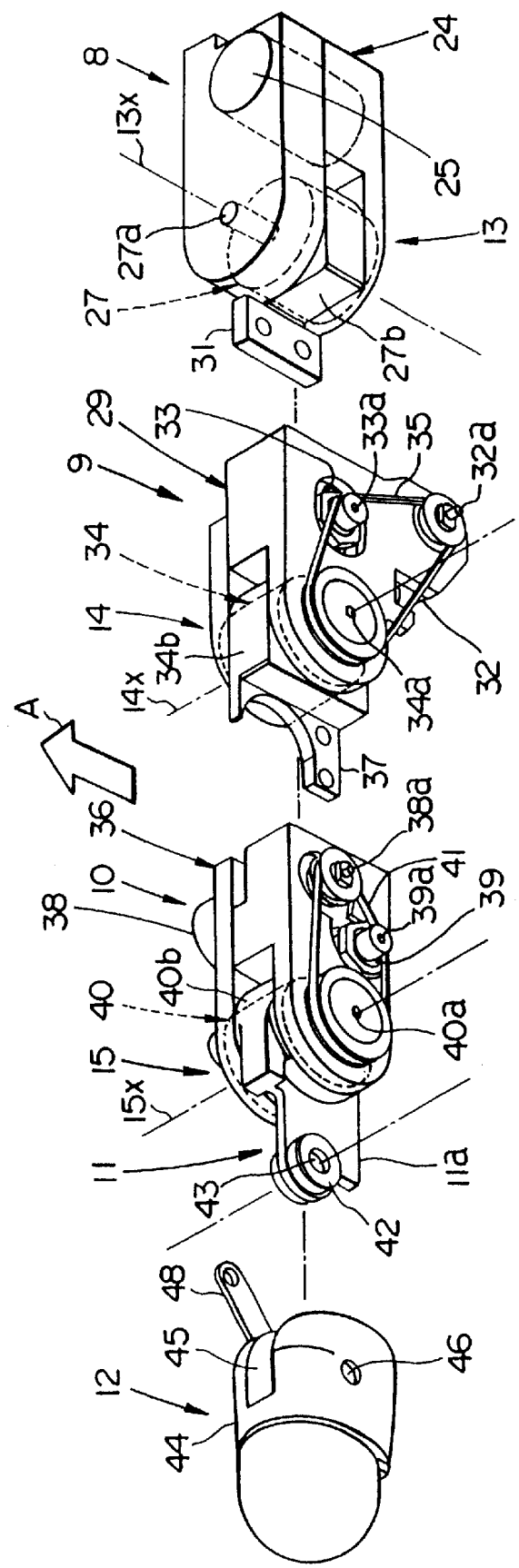
FIG. 5 is an exploded perspective view of a finger mechanism of the multifinger hand device shown in FIGS. 1 and 2.
Figure 6:
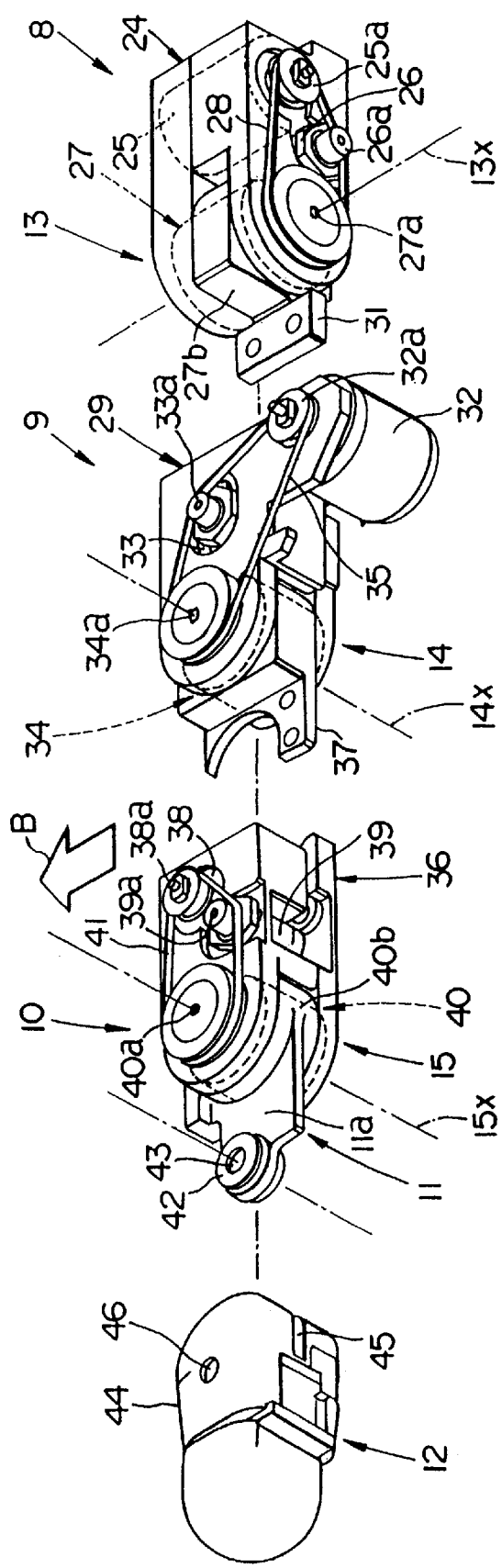
FIG. 6 is an exploded perspective view of the finger mechanism of the multifinger hand device shown in FIGS. 1 and 2.
Figure 7:
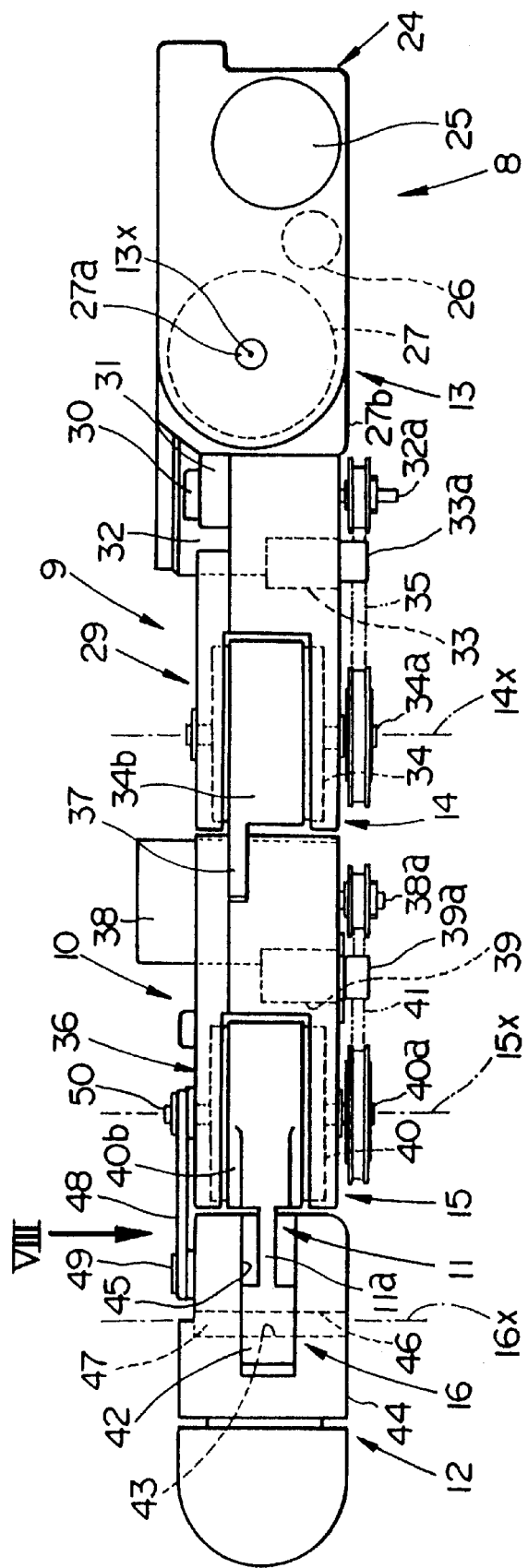
FIG. 7 is a plan view of the finger mechanism of the multifinger hand device shown in FIGS. 1 and 2.
Figure 8:
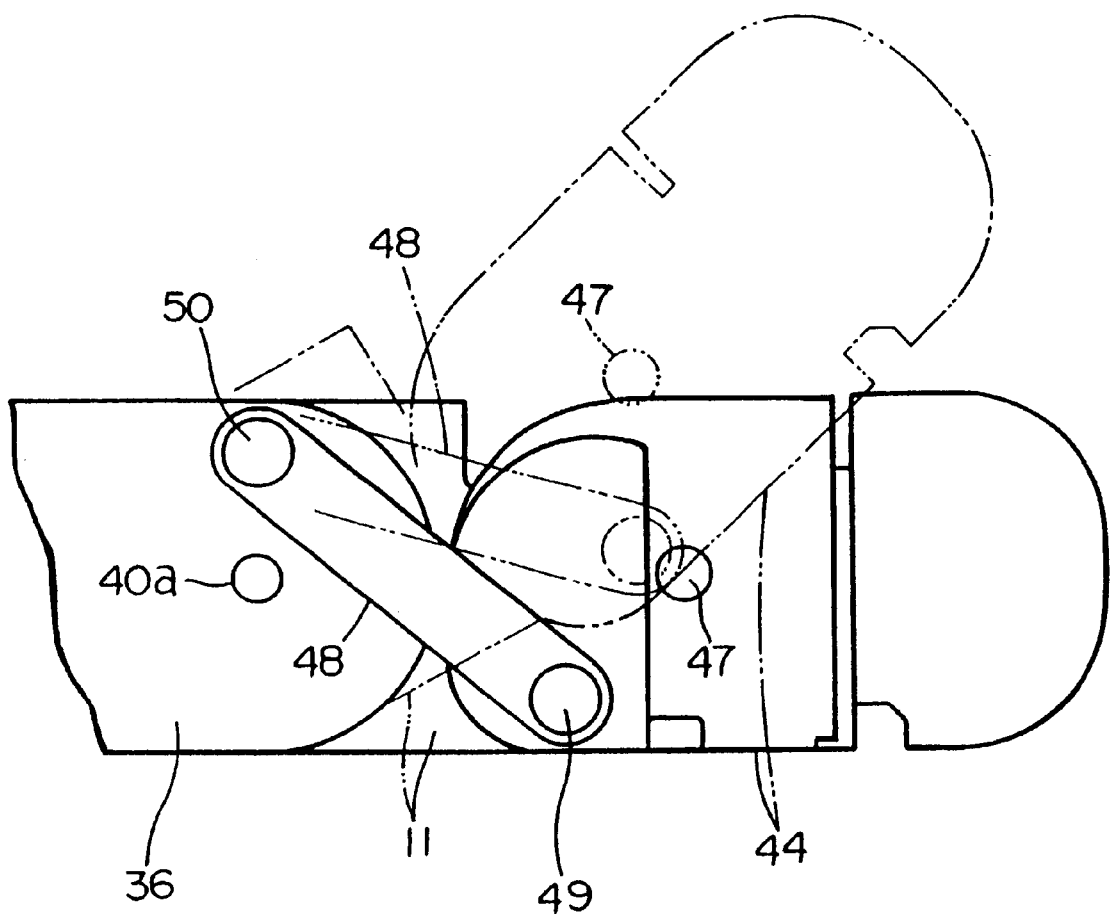
FIG. 8 is a view as viewed in the direction indicated by the arrow VIII in FIG. 7.

FIGS. 5 and 6 show in exploded perspective the finger mechanism 3, for example, among the identical finger mechanisms 3–5. In FIGS. 5 and 6, the components of the finger mechanism 3 are shown as disassembled at the joints 13–16. In FIG. 5, the finger mechanism 3 has its anterior side, which is the same side as the flat palm surface 6a of the palm unit 1 and faces the flat palm surface 6a when the finger mechanism 3 is bent as shown in FIGS. 1 and 2, shown facing upwardly in the direction indicated by the arrow A. In FIG. 6, the anterior side of the finger mechanism 3 is shown facing laterally in the direction indicated by the arrow B. FIG. 7 shows in plan the finger mechanism 3 as it is extended, and FIG. 8 shows a portion of the finger mechanism 3 as viewed in the direction indicated by the arrow VIII in FIG. 7.

As shown in FIGS. 5 through 7, the first link mechanism 8 of the finger mechanism 3 comprises a mechanism frame 24 of the first link mechanism 8 fixed to the palm unit 1, an electric motor 25 (actuator) mounted in the mechanism frame 24 for actuating the first joint 13, a rotary encoder 26 mounted in the mechanism frame 24 for detecting an angular displacement of the electric motor 25 or an operated position of the first joint 13, and a speed reducer 27 mounted in the mechanism frame 24 and comprising a planetary gear mechanism or the like. As shown in FIG. 6, the electric motor 25 has a drive shaft 25a operatively coupled to a rotatable shaft 26a of the rotary encoder 26 and an input shaft 27a of the speed reducer 27 by an endless belt 28. Therefore, rotation of the drive shaft 25a of the electric motor 25 can be transmitted to the rotatable shaft 26a of the rotary encoder 26 and the input shaft 27a of the speed reducer 27 by the endless belt 28.

The speed reducer 27, which constitutes the first joint 13, has a rotary output member 27b for outputting the rotation from the input shaft 27a at a speed reduction ratio. Specifically, the rotary output member 27b can be rotated about the rotational axis of the input shaft 27a, which is aligned with the rotational axis 13x of the first joint 13, at an angular speed lower than the input shaft 27a. The rotary output member 27b serves as a component of the second link mechanism 9, and has an integral connector 31 to which a mechanism frame 29 of the second link mechanism 9 is fastened by a screw 30. With the mechanism frame 29 of the second link mechanism 9 being fastened to the connector 31 by the screw 30, the mechanism frame 29 of the second mechanism 9 is integrally combined with the rotary output member 27b of the speed reducer 27. When the electric motor 25 of the first link mechanism 8 is energized, the second link mechanism 9 is angularly moved about the input shaft 27a of the speed reducer 27 that is aligned with the rotational axis 13x of the first joint 13.

As with the first link mechanism 8, the second link mechanism 9 comprises an electric motor 32 (actuator), a rotary encoder 33, and a speed reducer 34 which are mounted in the mechanism frame 29 that is coupled to the connector 31 of the rotary output member 27b. The electric motor 32 has a drive shaft 32a operatively coupled to a rotatable shaft 33a of the rotary encoder 33 and an input shaft 34a of the speed reducer 34 by an endless belt 35. The electric motor 32, the rotary encoder 33, and the speed reducer 34 are arranged such that their rotational axes extend perpendicularly to the rotational axis 13x of the first joint 13 with the mechanism frame 29 being coupled to the connector 31 of the first joint 13.

The speed reducer 34, which constitutes the second joint 14, has a rotary output member 34b for outputting the rotation from the input shaft 34a at a speed reduction ratio, the rotary output member 34b serving as a component of the third link mechanism 10, as with the speed reducer 27 of the first link mechanism 8. The rotary output member 34b can be rotated about the input shaft 34a of the speed reducer 34, which is aligned with the rotational axis 14x of the second joint 14, at an angular speed lower than the input shaft 34a. The rotary output member 34b has an integral connector 37 to which a mechanism frame 36 of the third link mechanism 10 is fastened by a screw, not shown. With the mechanism frame 36 of the third link mechanism 10 being thus fastened to the connector 37, when the electric motor 32 of the second link mechanism 9 is energized, the third link mechanism 10 is angularly moved in unison with the rotary output member 34b about the input shaft 34a of the speed reducer 34 that is aligned with the rotational axis 14x of the second joint 14.

As with the first link mechanism 8, the third link mechanism 10 comprises an electric motor 38 (actuator), a rotary encoder 39, and a speed reducer 40 which are mounted in the mechanism frame 36 that is coupled to the connector 37 of the rotary output member 34b. The electric motor 38 has a drive shaft 38a operatively coupled to a rotatable shaft 39a of the rotary encoder 39 and an input shaft 40a of the speed reducer 40 by an endless belt 41. The electric motor 38, the rotary encoder 39, and the speed reducer 40 are arranged such that their rotational axes extend parallel to the rotational axis 14x of the second joint 14 with the mechanism frame 36 being coupled to the connector 37 of the second link mechanism 9.

The speed reducer 40, which constitutes the third joint 15, has a rotary output member 40b for outputting the rotation from the input shaft 40a at a speed reduction ratio, the rotary output member 40b serving as a component of the fourth link mechanism 11, as with the speed reducer 27 of the first link mechanism 8. The rotary output member 40b can be rotated about the input shaft 40a of the speed reducer 40, which is aligned with the rotational axis 15x of the third joint 15, at an angular speed lower than the input shaft 40a. To the rotary output member 40b, there is integrally joined a plate-like body 11a of the fourth link mechanism 11. When the electric motor 38 of the third link mechanism 10 is energized, the fourth link mechanism 11 is angularly moved in unison with the rotary output member 40b about the input shaft 40a of the speed reducer 40 that is aligned with the rotational axis 15x of the third joint 15.

The body 11a of the fourth link mechanism 11 has a distal end, remote from the rotary output member 40b, supporting a connector 42 for connection to the fifth link mechanism 12. The connector 42 serves as a component of the fourth joint 16, and has a pin hole 43 defined therein whose rotational axis extends parallel to the rotational axis 15x of the third joint 15.

As shown in FIG. 7, the connector 42 is inserted in a groove 45 defined in an end of a mechanism frame 44 of the fifth link mechanism 12 which is closer to the fourth link mechanism 11. The pin hole 43 in the connector 42 is held in coaxial relation to a pin hole 46 defined in the mechanism frame 44 in a direction across the groove 45. A pin 47 is inserted through the pin hole 46 in the mechanism frame 44 and the pin hole 43 in the connector 42, thus coupling the connector 42 to the mechanism frame 44. The pin 47 by which the connector 42 is connected to the mechanism frame 44 serves as the fourth joint 16. The fifth link mechanism 12 is thus rotatable about the rotational axis of the pin 47 which is aligned with the rotational axis 16x of the fourth joint 16.

In the present embodiment, the mechanism frame 44 of the fourth link mechanism 12 is coupled to not only the connector 42 of the fourth link mechanism 11, but also the mechanism frame 36 of the third link mechanism 10 by an arm 48, as shown in FIG. 8.

The arm 48 extends obliquely to the longitudinal direction of the finger mechanism 3 from a rear end portion of a side of the mechanism frame 44 of the fifth link mechanism 12 to a front end portion of a side of the mechanism frame 36 of the third link mechanism 10. The arm 48 has its opposite ends rotatably supported respectively on the mechanism frames 44, 36 by respective pivot shafts 49, 50.

Because of the arm 48 interconnecting the mechanism frames 44, 36, when the electric motor 38 of the third link mechanism 10 is energized to turn the fourth link mechanism 11 toward the anterior side of the finger mechanism 3 as indicated by the imaginary lines in FIG. 8, the fifth link mechanism 12 is turned about the pin 47 with respect to the fourth link mechanism 11, and hence turned with respect to the third link mechanism 10 through an angle greater than the fourth link mechanism 11. Stated otherwise, when the finger mechanism 3 is bent toward its anterior side about the third joint 15, it is also bent toward its anterior side about the fourth joint 16 in unison with such bending motion about the third joint 15. Therefore, the electric motor 38 of the third link mechanism 10 serves as an actuator for operating the third joint 15 and also an actuator for operating the fourth joint 16.

Each of the finger mechanisms 4, 5 has a structure which is exactly identical to the structure of the finger mechanism 3 which has been described above. Though not shown in detail, the finger mechanism 2 has a structure ranging from the first link mechanism 17 to the third joint 23 which is exactly identical to the structure of the finger mechanisms 3–5 which ranges from the first link mechanism 8 to the third joint 15. Specifically, the first link mechanism 17, the second link mechanism 18, the third link mechanism 19, the first joint 21, the second joint 22, and the third joint 23 of the finger mechanism 2 are structurally identical to the first link mechanism 8, the second link mechanism 9, the third link mechanism 10, the first joint 13, the second joint 14, and the third joint 15 of each of the finger mechanisms 3–5.

Only the structure of the fourth link mechanism 20 of the finger mechanism 2, which is located more closely to the tip end thereof than the third joint 23, is different from the structure of the portion of each of the finger mechanisms 3–5 that is closer to the tip end than the third joint 15. The fourth link mechanism 20 of the finger mechanism 2 does not have the arm 48 of each of the finger mechanisms 3–5, but has such a structure similar to the fourth and fifth link mechanisms 11, 12, integrally fastened together by screws, of each of the finger mechanisms 3–5.

The multifinger hand device constructed as described above operates and offers advantages as follows:

It is assumed that from the extended state of the finger mechanisms 2–5, i.e., from the spread state of the multifinger hand device, the second link mechanism 18 of the finger mechanism 2 is turned about the rotational axis 21x of the first joint 21 to orient the second link mechanism 18 in the same direction as the rotational axis 13x of the first joint 13 of the finger mechanism 4, the second mechanism 9 of the finger mechanism 4 is turned about the rotational axis 13x of the first joint 13 to orient the second mechanism 9 in the same direction as the rotational axis 21x of the first joint 21 of the finger mechanism 2, and the third link mechanism 10 of the finger mechanism 4 is turned about the rotational axis 14x of the second joint 14 to orient the third link mechanism 10 in the same direction as the rotational axis 13x of the first joint 13 of the finger mechanism 4.

Figure 9B:
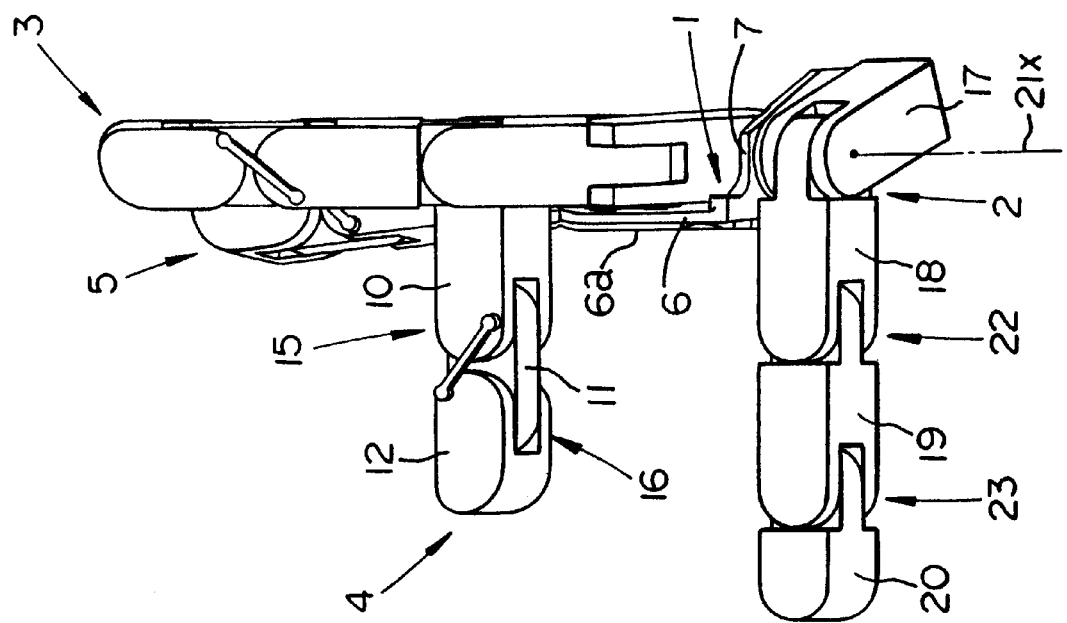
FIG. 9(b) is a perspective view showing the example of operation of the multifinger hand device which is illustrated in FIG. 9(a)
Figure 9A:
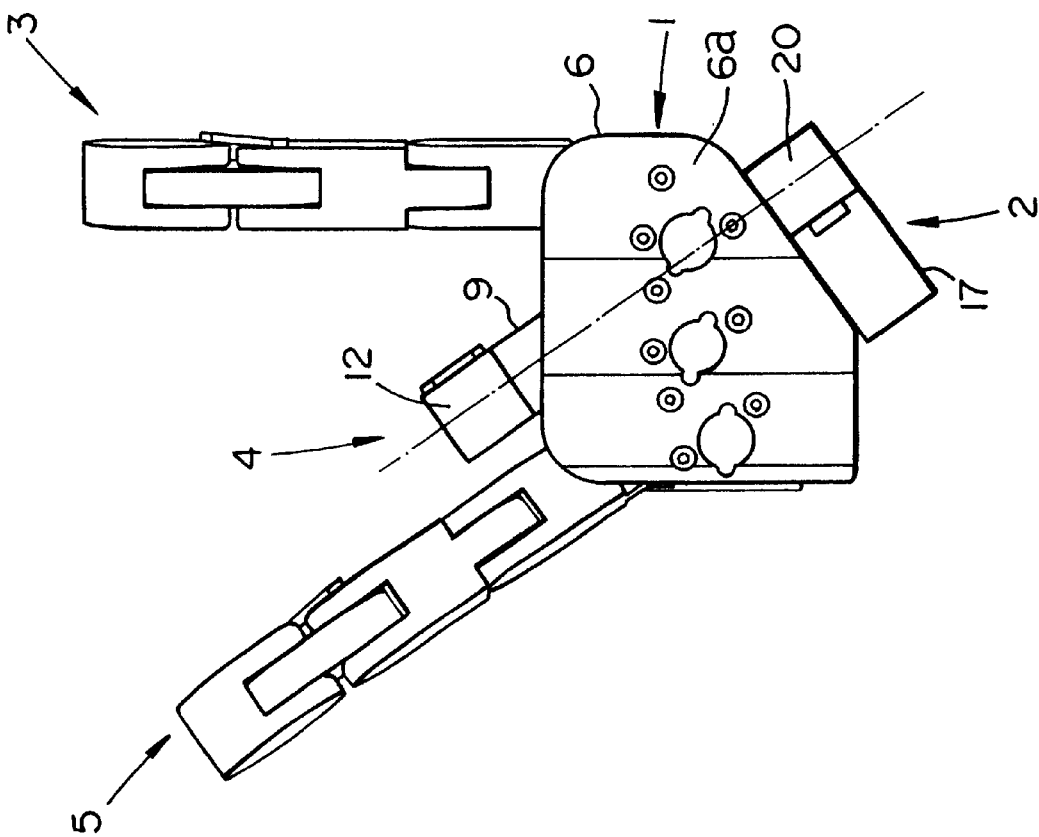
FIG. 9(a) is a plan view showing an example of operation of the multifinger hand device shown in FIGS. 1 and 2.

Since the rotational axis 21x of the joint 21 of the finger mechanism 2 is substantially perpendicular to the rotational axis 13x of the joint 13 of the finger mechanism 4, as shown in FIGS. 9(a) and 9(b), the portion of the finger mechanism 2 which is closer to the tip end than the first joint 21, i.e., which ranges from the second link mechanism 18 to the fourth link mechanism 20, and the portion of the finger mechanism 4 which is closer to the tip end than the second joint 14, i.e., which ranges from the third link mechanism 10 to the fifth link mechanism 12, lie in the same plane and have their anterior sides facing each other. FIG. 9(a) shows in plan the multifinger hand device with the finger mechanisms 2, 4 thus operated, as viewed from the flat palm surface 6a in the direction of the rotational axis 13x of the first joint 13 of the finger mechanism 4. FIG. 9(b) shows in perspective the multifinger hand device with the finger mechanisms 2, 4 thus operated.

Inasmuch as the finger mechanisms 2, 4 can thus be brought into facing relation to each other, the multifinger hand device can reliably grasp an object, not shown, between the finger mechanisms 2, 4. At this time, the finger mechanism 4 is turned about the rotational axis 13x of the first joint 13 toward the finger mechanism 5. However, the finger mechanism 15 may be turned about the rotational axis 13x of the first joint 13 easily out of physical interference with the finger mechanism 4 thus turned.

It is also assumed that from the position shown in FIGS. 9(a) and 9(b), the finger mechanism 5 is slightly turned about the rotational axis 13x of the first joint 13 in a direction away from the finger mechanism 4, the finger mechanism 3 is turned about the rotational axis 13x of the first joint 13 in a direction toward the finger mechanism 4, the second through fourth joints 14–16 of the finger mechanisms 3–5 are operated to bend the tip ends of the finger mechanisms 3–5 toward the finger mechanism 2, and the second and third joints 22, 23 of the finger mechanism 2 are operated to bend the tip end of the finger mechanism 2 toward the finger mechanism 4. The finger mechanisms 2–5 thus operated are shown in FIGS. 1 through 3.

At this time, since the first joints 13 of the finger mechanisms 3–5 are inclined to each other as shown in FIG. 4, the tip ends of the finger mechanisms 3–5 are brought closely together (see FIG. 1). Therefore, the multifinger hand device can grasp an object (not shown) between the finger mechanisms 3–5 and the finger mechanism 2.

In the present embodiment, the first link mechanisms 8 of the finger mechanisms 3–5 which are fixed to the palm unit 1 extend radially toward the tip ends of the finger mechanisms 3–5, as shown in FIG. 3. Therefore, the portions of the finger mechanisms 3–5 which are closer to the tip ends than the first joints 13, i.e., which range from the second link mechanisms 9 to the fifth link mechanisms 12, can rotate in a relatively wide angular range about the respective rotational axes 13x of the first joints 13 on both sides of the central axes C3, C4, C5 of the first link mechanisms 8. Therefore, the finger mechanisms 3–5 can be operated into a state shown in FIGS. 10(a) and 10(b).

Figure 10A:
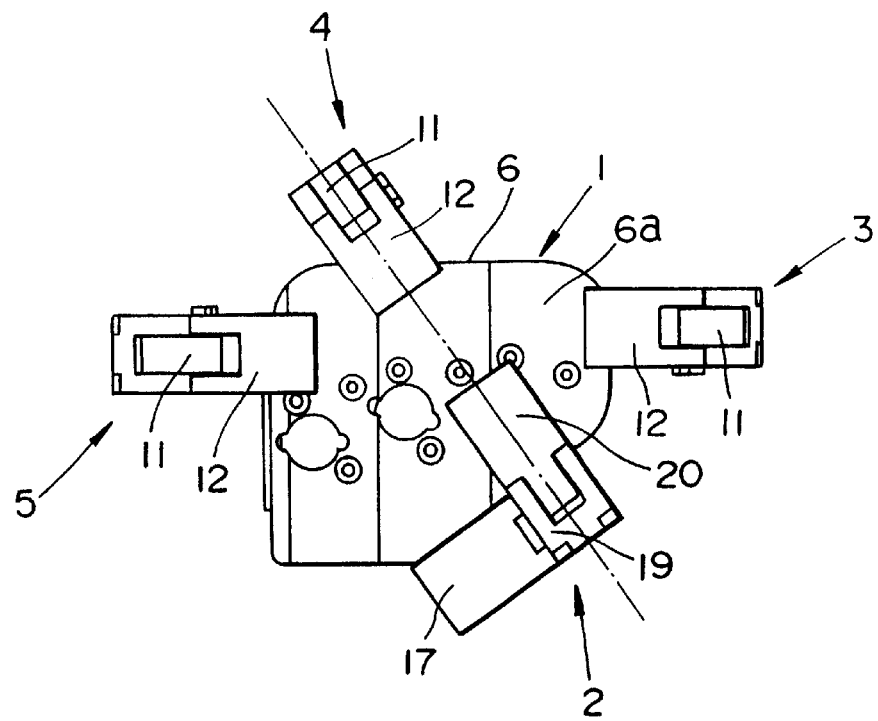
FIG. 10(a) is a plan view showing an example of operation of the multifinger hand device shown in FIGS. 1 and 2.
Figure 10B:
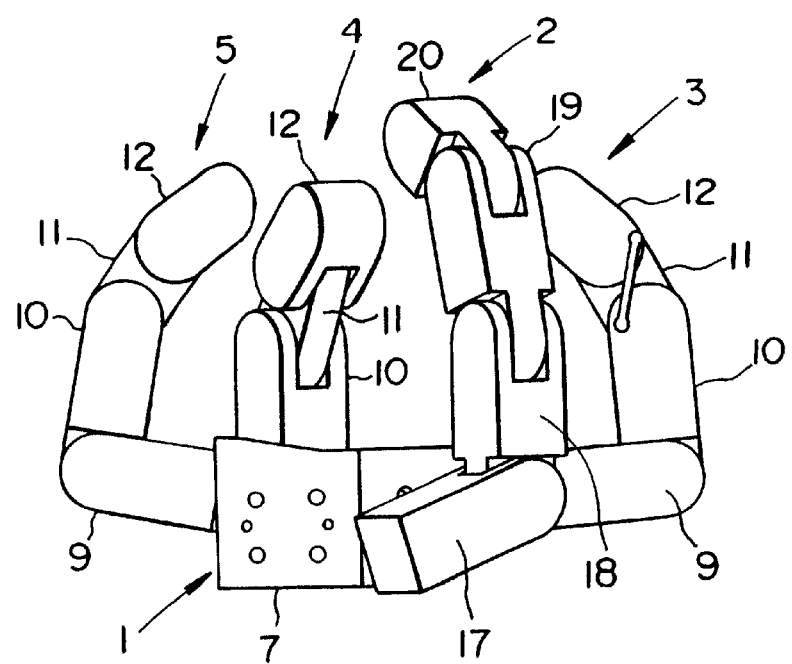
FIG. 10(b) is a perspective view showing the example of operation of the multifinger hand device which is illustrated in FIG. 10(a).

FIGS. 10(a) and 10(b) show the multifinger hand device with the finger mechanisms 3, 5 facing each other transversely across the palm unit 1 by operating the first joint 13 of the finger mechanism 3 to turn the finger mechanism 3 away from the finger mechanism 4 and also operating the first joint 13 of the finger mechanism 5 to turn the finger mechanism 5 away from the finger mechanism 4. In FIG. 10(a), the multifinger hand device thus operated is viewed from the flat palm surface 6a of the palm unit 1 in the direction of the rotational axis 13x of the first joint 13 of the finger mechanism 4. In FIG. 10(b), the multifinger hand device thus operated is viewed in perspective.

When the finger mechanisms 2–5 are thus operated, the multifinger hand device can grasp an object (not shown) between the finger mechanisms 2, 4 in a direction and also between the finger mechanisms 3, 5 in a direction different from the above direction. Therefore, the multifinger hand device can grasp the object reliably.

Since the finger mechanisms 3–5 of the multifinger hand device are identical in structure, they can be switched around or can replace each other. Therefore, the inventory control for the finger mechanisms 3–5 in factories for producing multifinger hand devices and working shops for processing multifinger hand devices can be facilitated. When either one of the finger mechanisms 3–5 is broken, it can easily be replaced with a new one of the other finger mechanisms.

In the above embodiment, the multifinger hand device with the four finger mechanisms 2–5 has been described. However, the multifinger hand device according to the present invention may have a different number of finger mechanisms, e.g., may have five finger mechanisms as with a human hand.

In the above embodiment, the finger mechanism 2 which corresponds to the thumb of a human hand is structurally different from the finger mechanisms 3–5 with respect to their tip ends. However, the tip end of the finger mechanism 2 may be identical in structure to the tip ends of the finger mechanisms 3–5.

In the above embodiment, actuators (electric motors) for operating, e.g., bending, the finger mechanisms 2–5 are installed in the finger mechanisms 2–5. However, such actuators may be installed in the palm unit of the multifinger hand device or in an arm connected to the palm unit of the multifinger hand device. In such a modification, the rotational power may be transmitted from the actuators to the finger mechanisms 2–5 by rotation transmitting means comprising wires, pulleys, speed reducers, etc.

Although a certain preferred embodiment of the present invention has been shown and described in detail, it should be understood that various changes and modifications may be made therein without departing from the scope of the appended claims.

What is claimed is:

1. A multifinger hand device comprising:
   a palm unit; and
   a plurality of finger mechanisms extending from said palm unit, each of said finger mechanisms comprising a plurality of link mechanisms successively joined from said palm unit by a plurality of joints;
   said finger mechanisms including a finger mechanism corresponding to a thumb and other finger mechanisms, the joints of said other finger mechanisms include first joints closest to said palm unit, said first joints being juxtaposed substantially transversely across said palm unit and having respective rotational axes about which the first joints are rotatable and which are oriented substantially perpendicularly to a flat palm surface of said palm unit, and wherein the link mechanisms of said other finger mechanisms include link mechanisms coupled to said first joints and closest to said palm unit, said link mechanisms being fixed to said palm unit such that transversely central axes thereof are inclined to each other and extend toward respective tip ends of said other finger mechanisms.

2. The multifinger hand device according to claim 1, wherein said first joints are arranged with their rotational axes inclined to each other in a direction substantially perpendicular to the flat palm surface of said palm unit, and spreading radially toward a back of said palm unit.

3. The multifinger hand device according to claim 1, wherein said other finger mechanisms include at least two finger mechanisms which are structurally identical to each other.

4. The multifinger hand device according to claim 1 for 3, further comprising:
   a plurality of actuators mounted respectively in said finger mechanisms for rotating the joints of the finger mechanisms.

5. A multifinger hand device comprising:
   a palm unit; and
   a plurality of finger mechanisms extending from said palm unit, each of said finger mechanisms comprising a plurality of link mechanisms successively joined from said palm unit by a plurality of joints;
   said finger mechanisms including a finger mechanism corresponding to a thumb and other finger mechanisms, the joints, which are closest to said palm unit, of said other finger mechanisms being juxtaposed substantially transversely across said palm unit and having respective rotational axes about which the joints are rotatable, said joints being arranged with their rotational axes inclined to each other in a direction substantially perpendicular to a flat palm surface of said palm unit, and spreading radially toward a back of said palm unit.

6. The multifinger hand device according to claim 5, wherein said other finger mechanisms include at least two finger mechanisms which are structurally identical to each other.

7. The multifinger hand device according to claim 5 or 6, further comprising:
   a plurality of actuators mounted respectively in said finger mechanisms for rotating the joints of the finger mechanisms.

8. A multifinger hand device comprising:
   a palm unit; and
   a plurality of finger mechanisms extending from said palm unit, each of said finger mechanisms comprising a plurality of link mechanisms successively joined from said palm unit by a plurality of joints;
   said finger mechanisms including a thumb mechanism and other finger mechanisms, first joints, which are closest to said palm unit, of said thumb mechanism and at least one of said other finger mechanisms being arranged such that a rotational axis about which said first joint of the thumb mechanism is rotatable and a rotational axis about which said first joint of said at least one of the other finger mechanisms is rotatable cross each other,
   wherein said first joints of said other finger mechanisms are juxtaposed substantially transversely across said palm unit,
   said rotational axes of said first joints of the other finger mechanisms are oriented substantially perpendicularly to a flat palm surface of the palm unit, and
   said link mechanisms of the other finger mechanisms are fixed to said palm unit such that transversely central axes thereof are inclined to each other and extend toward respective tip ends of the other finger mechanisms.

9. A multifinger hand device comprising:
   a palm unit; and a plurality of finger mechanisms extending from said palm unit, each of said finger mechanisms comprising a plurality of link mechanisms successively joined from said palm unit by a plurality of joints;

said finger mechanisms including a thumb mechanism and other finger mechanisms, first joints, which are closest to said palm unit, of said thumb mechanism and at least one of said other finger mechanisms being arranged such that a rotational axis about which said first joint of the thumb mechanism is rotatable and a rotational axis about which said first joint of said at least one of the other mechanisms is rotatable cross each other, wherein said first joints of said other finger mechanisms are juxtaposed substantially transversely across said palm unit, said rotational axes of said first joints of the other finger mechanisms are inclined to each other in a direction substantially perpendicular to a flat palm surface of said palm unit, and spread radially toward a back of said palm unit.

10. A multifinger hand device according to claim 8 or 9, wherein said other finger mechanisms include at least two finger mechanisms which are structurally identical to each other.

11. A multifinger hand device according to claim 8 or 9, further comprising:

a plurality of actuators mounted respectively in said finger mechanisms for rotating the joints of the finger mechanisms.

12. A multifinger hand device comprising:

a palm unit; and a plurality of finger mechanisms extending from the palm unit, each of the finger mechanisms comprising a plurality of link mechanisms successively joined from the palm unit by a plurality of joints;

wherein the finger mechanisms include a thumb mechanism and a specific finger mechanism, first joints, which are closest to the palm unit, of the thumb and specific finger mechanisms being arranged such that a rotational axis about which the first joint of the thumb mechanism is rotatable and a rotational axis about which the first joint of the specific finger mechanism is rotatable are substantially orthogonal to each other; and the link mechanisms of the thumb and specific finger mechanisms can be in a same plane and face each other by rotation of the first joint of at least one of the thumb and specific finger mechanisms.

13. The multifinger hand device according to claim 12, wherein each of the thumb and specific finger mechanisms comprises other joints than the first joint, each of the other joints of the thumb and specific finger mechanisms has a one degree of freedom, and rotational axes of the other joints of the thumb and specific finger mechanisms can run parallel to each other by rotation of the first joint of at least one of the thumb and specific finger mechanisms.

14. The multifinger hand device according to claim 13, wherein the rotational axes of the first and other joints of the thumb mechanism are substantially perpendicular, and the rotational axes of the first and other joints of the specific finger mechanism are substantially perpendicular.

15. The multifinger hand device according to claim 13, wherein each of the thumb and specific finger mechanisms comprises a plurality of the other joints, the rotational axes of the other joints of the thumb mechanism are parallel to each other, and the rotational axes of the other joints of the specific finger mechanism are parallel to each other.

16. The multifinger hand device according to claim 12, wherein the finger mechanisms include a pair of finger mechanisms other than the thumb and specific finger mechanisms, the pair of finger mechanisms having first joints, which are closest to the palm unit, arranged such that rotational axes about which the first joint of each of the pair of the finger mechanisms are rotatable are substantially parallel to each other, and the link mechanisms of the pair of the finger mechanisms can be in a same plane and face each other by rotation of the first joint of at least one of the pair of the finger mechanisms.

17. The multifinger hand device according to claim 16, wherein the first joints of the specific finger mechanism and the pair of the finger mechanisms are juxtaposed substantially transversely across the palm unit, the rotational axes of the first joints of the specific finger mechanism and the pair of the finger mechanisms are oriented substantially perpendicularly to a flat palm surface of the palm unit, and the link mechanisms of the specific finger mechanism and the pair of the finger mechanisms are fixed to the palm unit such that transversely central axes thereof are inclined to each other and extend toward respective tip ends of the specific finger mechanism and the pair of the finger mechanisms.

18. The multifinger hand device according to claim 16, wherein the first joints of the specific finger mechanism and the pair of the finger mechanisms are juxtaposed substantially transversely across the palm unit, the rotational axes of the first joints of the specific finger mechanism and the pair of the finger mechanisms are inclined to each other in a direction substantially perpendicularly to a flat palm surface of the palm unit, and spread radially toward a back of the palm unit.

19. The multifinger hand device according to claim 16, wherein at least two of the specific finger mechanisms and the pair of the finger mechanisms are structurally identical to each other.

20. The multifinger hand device according to claim 12, further comprising:

a plurality of actuators mounted respectively in the finger mechanisms for rotating the joints of the finger mechanisms.

* * * * *